United States Patent [19]
Clifton et al.

[11] Patent Number: 6,113,626
[45] Date of Patent: Sep. 5, 2000

[54] HEAT TRANSFER BLANKET FOR CONTROLLING A PATIENT'S TEMPERATURE

[75] Inventors: Guy L. Clifton; Emmy R. Miller, both of Houston, Tex.

[73] Assignee: The Board of Regents of the University of Texas System, Austin, Tex.

[21] Appl. No.: 09/065,156

[22] Filed: Apr. 23, 1998

[51] Int. Cl.⁷ ........................................ A61F 7/00
[52] U.S. Cl. ........................... 607/96; 607/104; 607/108; 607/114
[58] Field of Search .............................. 607/96, 104, 108, 607/111, 114

[56] References Cited

U.S. PATENT DOCUMENTS

| | | |
|---|---|---|
| 2,093,834 | 9/1937 | Gaugler . |
| 2,110,022 | 3/1938 | Kliesrath ........................................ 5/334 |
| 2,512,559 | 6/1950 | Williams ........................................ 5/347 |
| 2,938,356 | 5/1960 | McMahon ........................................ 62/3 |
| 2,991,627 | 7/1961 | Suits ................................................ 62/3 |
| 3,112,792 | 12/1963 | Coleman et al. ........................... 165/46 |
| 3,154,926 | 11/1964 | Hirschorn ........................................ 62/3 |
| 3,211,216 | 10/1965 | Coleman et al. ........................... 165/46 |
| 4,017,921 | 4/1977 | Hernandez .................................... 5/347 |
| 4,094,357 | 6/1978 | Sgroi .............................................. 165/105 |
| 4,114,620 | 9/1978 | Moore et al. . |
| 4,118,946 | 10/1978 | Tubin ............................................. 62/514 |
| 4,132,262 | 1/1979 | Wibell ........................................... 165/26 |
| 4,149,541 | 4/1979 | Gammons et al. . |
| 4,353,359 | 10/1982 | Milbauer ..................................... 601/166 |
| 4,660,388 | 4/1987 | Greene, Jr. .................................... 62/261 |
| 4,662,433 | 5/1987 | Cahn et al. .................................... 165/46 |
| 4,859,250 | 8/1989 | Buist ............................................. 136/225 |
| 5,014,695 | 5/1991 | Benak et al. . |
| 5,125,238 | 6/1992 | Ragan et al. ............................... 62/259.3 |
| 5,165,127 | 11/1992 | Nicholson ..................................... 5/421 |
| 5,265,599 | 11/1993 | Stephenson et al. ...................... 607/104 |
| 5,392,847 | 2/1995 | Stephenson ................................. 165/46 |
| 5,486,204 | 1/1996 | Clifton ........................................ 607/96 |
| 5,785,716 | 7/1998 | Bayron et al. ............................. 607/108 |

OTHER PUBLICATIONS

Michael McEwan "*Hypothermia–physiology, Signs, Symptioms and Treatment Considerations*", Search and Rescue Society of British Columbia, 1995.

Stiff and Sixta, "*Hypothermia Care and Prevention*", 1997.

Mortensen et al "Colorectal Surgery Comes in From the Cold", The New England Journal of Medicine, vol. 334, No. 19, May 19, 1996.

*Primary Examiner*—Linda C. M. Dvorak
*Assistant Examiner*—R. Kearney
*Attorney, Agent, or Firm*—J. M. (Mark) Gilbreth; Gilbreth & Associates P.C.

[57] ABSTRACT

The present invention relates to a heat transfer blanket which wraps the torso and legs leaving the arms, buttocks, perineum and head exposed and allows for the selective heating or cooling of various body parts at the same or different rates. The blanket of the present invention is also made up of panels which may be selectively opened to gain access to the chest, abdomen, legs or back to expose a surgical field or to provide access to these areas for necessary medical care.

20 Claims, 9 Drawing Sheets

HEAT TRANSFER BLANKET FOR CONTROLLING A PATIENT'S TEMPERATURE

BACKGROUND OF THE INVENTION

1. Field of the Invention

The present invention relates to a heat transfer system for and method of controlling a patient's temperature. In another aspect, the present invention relates to a heat transfer blanket for and method of controlling a patient's temperature. In even another aspect, the present invention relates to a heat transfer blanket for controlling a patient's temperature where in the heat transfer blanket comprises independently controlled zones for heating and cooling, and a method for heating and cooling various parts of a patient at different temperatures and rates.

2. Description of the related Art

Man is considered to be a tropical animal, with normal functioning requiring a body temperature of about 37° C. Relying only upon that protection from temperature stress which is provided physiologically at birth, comfortable human survival would require an environment of 37° C., +/− perhaps 1°. See, "Hypothermia-physiology, Signs, Symptoms and Treatment Considerations", Search and Rescue Society of British Columbia, compiled by Michael McEwan, 1995. The McEwan article further notes that a body can self-compensate for small upward or downward variations in temperature through the activation of a built-in thermal regulatory system, controlled by temperature sensors in the skin.

For example, the response to an upward variation in body temperature is the initiation of perspiration, which moves moisture from body tissues to the body surface, where evaporation causes cooling. Likewise, the response to a downward variation in body temperature is shivering, which is the body's involuntary contraction and expansion of muscle tissue on a large scale in an attempt to generate heat.

Stiff and Sixta, "Hypothermia Care and Prevention", 1997, generally define hypothermia as occurring when the body's core temperature drops below its normal 37° C.

The McEwan article defines impending hypothermia as occurring when the core temperature decreases to 36° C.

In the early stages mild hypothermia causes vigorous shivering which is usually accompanied by an increase in pulse and breathing rates. Cold, white hands and feet (as the blood vessels in the skin constrict) are the first signs of blood being shunted away from the body's extremities.

The McEwan article describes mild hypothermia as occurring when the core temperature is dropped to the range of 34–35° C. At this point, uncontrolled, intense shivering begins, although the victim is still alert and able to help self, however, movements become less coordinated and the coldness is creating some pain and discomfort.

The McEwan article defines moderate hypothermia as occurring when the core temperature is in the range of 31 to 33° C. At this point shivering slows or stops, muscles begin to stiffen and mental confusion and apathy sets in. Speech becomes slow, vague and slurred with breathing becoming slower and shallower.

The McEwan article defines severe hypothermia as occurring when the core temperature is below 31° C., with Stiff and Sixta defining severe hypothermia as resulting when the body temperature drops below 33° C. Shunting of the blood continues, manifesting as bluish lips and finger tips from poor oxygenation of the tissues near the body surface. Decreased circulation as results in a build-up of acid metabolites (waste products) in the muscles of the extremities until shivering stops and is replaced by muscular rigidity. The pulse and respirations begin to slow as the body core cools to 30° C. The heart may stop at temperatures of about 28° C. or less.

Hypothermia can occur easily enough during any outdoor excursion, especially in wilderness situations where weather conditions may deteriorate unexpectedly or where travelers may become lost, injured or exhaust food supplies prematurely. Additionally, outdoor activities involving water presents the added possibility of emersion with the body cooling up to 25 times faster in water than in air.

Mild hypothermia is also a common occurrence during major surgery on the upper body. The usual causes of such perioperative hypothermia or anesthetic-induced impairment of thermal regulation, exposure to cold, and altered distribution of body heat. This is particularly a problem in patients anesthetized for over two hours in where there are large incisions exposing the body's interior to room temperature. Routine measures to reduce heat loss during operation include covering the skin, warming intravenous fluid and transfused blood, and increasing ambient temperature. In most operations, with the exception of those on the brain prevention of hypothermia is a mainstay of anesthetic management because hypothermia during surgery can adversely affect the outcome. See "Colorectal Surgery Comes in From the Cold", The New England Journal of Medicine, Vol. 334, No. 19, Mortensen, et al, May 19, 1996.

As discussed above, hypothermia may be encountered as a result of an accident or may by inadvertently acquired during major surgery. In an odd twist, hypothermia may be induced by a physician in the treatment of various conditions usually those in which the physician desires to protect the brain or heart. For example, U.S. Pat. No. 5,486,204, issued Jan. 23, 1996 to Clifton discloses a method of treating a non-penetrating head wound with hypothermia. Such a treatment protocol includes specific defined times, temperatures, rates of change of temperature and the timing of the introduction of medications, and controlled rewarming. Additionally, hypothermia is frequently induced during surgery for intracranial aneurysms.

The McEwan article notes that treatment of cold injuries has long been controversial. It is also clear that it is not enough merely to reheat a victim suffering from hypothermia, but that controlled heating must be applied. For example, Baron Larrey, Napoleon's Chief Surgeon observed that those soldiers, suffering from hypothermia, who were placed closest to the campfire during Napoleon's retreat from Russian died. These soldiers probably rewarmed rapidly. As a general principle initial management principles for treating hypothermia emphasized prevention of further heat loss, rewarming as soon as it is safely possible at a "successful" rate (slowly) and rewarming the core before the shell in an attempt to avoid inducing lethal side effects during rewarming. This treatment goal is noted as being important, since hypothermia itself may not be fatal above 25° C. core temperature. Fatalities at 25° C. or greater normally occur during rewarming.

The McEwan article notices that hypothermia causes several reactions within the body as it tries to protect itself and retain its heat, the most important of these being vasoconstriction, which halts blood flow to the extremities in order to conserve heat in the critical core area of the body. Shivering is noted as maintaining peripheral vasoconstriction, which minimizes the severity of vascular collapse during rewarming. Induction of vasodilation in hypothermia patients may precipitate rewarming shock and metabolic acidosis. This may occur where the periphery (legs and arms) are warmed before the core (heart and lungs) are warmed. Furthermore, the rapid shunting of cold blood from the extremities to the core as a direct result of vasodilation may cause the core temperature to drop. Prevention of vasodilation is the reason why it is imperative that the hypothermia victim's extremities not be rewarmed before the core. If vasodilation occurs, cold blood returning to the heart may be enough to put the patient into ventricular fibrillation. Again see, the McEwan article.

The McEwan article notes treatment for the different levels of hypothermia. According to McEwan, treatment for mild hypothermia includes keeping the head and neck covered. Stiff and Sixta note that treatment for mild hypothermia generally includes application of hot packs, water bottles, or warm campfire rocks wrapped in hot, wet towels to the groin, head, neck and sides of the chest. McEwan that treatment for moderate hypothermia includes keeping the head and neck covered, with mild heat applied to the head, neck, chest, armpits and groin of the hypothermia patient. For severe hypothermia, McEwan notes that treatment includes application of heat by skin to skin contact in the areas of the chest and neck with exhaled warm air or steam introduced near the patient's nose and mouth. Stiff and Sixta note that treatment for severe hypothermia will include application of hot packs to the neck, armpits, sides of chest and groin of the hypothermia victim, with the head kept covered.

The following patents relate to various apparatus for applying heat or cooling to a patient.

U.S. Pat. No. 2,093,834, issued Sep. 21, 1937 to Gaugler, discloses a refrigerating apparatus for use with a bed which generally includes a blanket having a plurality of ducts into which a cooling or heating medium is provided to either cool or heat a person lying in a bed.

U.S. Pat. No. 2,110,022, issued Mar. 1, 1938 to Kliesrath, discloses a bed cover in which a heating or cooling medium is circulated.

U.S. Pat. No. 2,512,559, issued Jun. 20, 1950 to Williams, discloses a pad or blanket or the like which is associated with a heat transfer unit for heating or cooling a person lying in a bed.

U.S. Pat. No. 2,938,356, issued May 31, 1960 to McMahon, discloses bedding in the form of sheets, blankets or mattresses, or a flying suit, which may be utilized to heat or cool an individual using the bedding or flying suit. The bedding or flying suit may be described as a flexible supporting material of low conductivity which has embedded in it two types of segments each type of which is at least semi-conductive. A direct current is passed through this material in such a manner that heat will be absorbed or given off at junctions depending upon the direction of the current.

U.S. Pat. No. 2,991,627, issued Jul. 11, 1961 to Suits, discloses a cooling and heating blanket which may be placed in close proximity to a human body. The cooling and heating blanket utilizes a plurality of Peltier junctions through which direct electrical current is passed to obtain heating or cooling. This Peltier effect may be enhanced by circulating air through the blanket in a flexible tube.

U.S. Pat. No. 3,112,792, issued Dec. 3, 1963 to Coleman, et al, discloses a personal thermal device which is essentially a full body suit through which a heat transfer fluid is circulated throughout. The design of the '792 patent does not allow differential heating and cooling capability or exposed body parts for access for medical procedures.

U.S. Pat. No. 3,154,926, issued Nov. 3, 1964 to Hirschhorn, discloses, discloses a cooling blanket in which cold fluid is pumped through a plurality of rigid metal tubes.

U.S. Pat. No. 3,211,216, issued Oct. 12, 1965, to Coleman, et al, is a divisional of earlier described patent U.S. Pat. No. 3,112,792.

U.S. Pat. No. 4,094,357, issued Jun. 13, 1978, to Sgroi, discloses a heat transfer blanket having a plurality of flexible heat pipe sandwich between the outer most layers of the blanket.

U.S. Pat. No. 4,017,921, issued Apr. 19, 1977, to Hernandez, discloses a cooling blanket which utilizes a plurality of elongated chambers defined normally by a plurality of elongated joints between the blanket lamina, wherein the chambers are adapted for receiving ice.

U.S. Pat. No. 4,114,620, issued Sep. 19, 1978, to Moore, et al, discloses a patient treatment pad for hot or cold use which utilizes a pair of laminated plastic film panels defining a passage there between for circulating hot or cold water.

U.S. Pat. No. 4,118,946, issued Oct. 10, 1978, to Tubin, discloses a flexible sheet or garment to be worn on or around the human body, or body member for cooling, which flexible sheet or garment a viscous liquid heat transfer media in a first fluid path and a pressurized gas in a second fluid path to transfer heat away from the body. The '946 device, however, is to be worn in situations of high external temperature and is not suited for medical applications where very precise control of the temperature of an injured or ill person who cannot auto regulate their own temperature is desired. Also, the '946 devise's rectangular shape that does not conform to the body.

U.S. Pat. No. 4,132,262, issued Jan. 2, 1979, to Wibell, discloses a heating and cooling blanket with heating means including a plurality of flexible elements positioned within the blanket for being electrically energized for supplying heat to the blanket, and cooling means including plurality of flexible fluid carrying conduits positioned within the blanket to which a heat transfer fluid can flow, such that the blanket may be retained below room temperature. These heating and cooling elements are provided in such a manner as to provide a thermal blanket having respective independently controllable zones, such that the zones may either concurrently heat and cool the user of the blanket. The '262 invention discloses zones which may be independently heated and cooled. However, the zones of the '262 device are rectangular zones in a rectangular blanket which neither conforms to the body nor provides access to the body for surgery or medical care.

U.S. Pat. No. 4,149,541, issued Apr. 17, 1979, to Gammons, et al, discloses a fluid circulating pad with interconnecting internal passages for (circulating a hot or cold liquid for treating a patient.

U.S. Pat. No. 4,660,388, issued Apr. 28, 1987, to Greene, Jr., discloses a cooling cover comprising a plurality of small air jets through which air is directed onto the body of a user of the cooling cover.

U.S. Pat. No. 4,662,433, issued May 5, 1987, to Cahn, et al, discloses a cooling blanket which utilizes a stable circulating foam as the cooling medium.

U.S. Pat. No. 4,859,250, issued Aug. 22, 1989, to Buist, discloses a thermal electric heat pump or power source device which is provided with P-type and N-type elements made of either thin films or thick films for use on flexible or nonflexible substrates such as thermals, blankets or therapeutic devices for heating or cooling.

U.S. Pat. No. 5,014,695, issued May 14, 1991, to Benak, et al, discloses a cooling/warming jacket pad for the containment of physiological organs; such as hearts and kidneys during medical procedures. The jacket of the '695 patent, however, is designed to wrap around an organ inside the body.

U.S. Pat. No. 5,125,238, issued Jun. 30, 1992, to Ragan, et al, discloses a disposable patient heating or cooling blanket. The patient is bathed and conditioned air through a multiplicity of orifices in the bottom layers of the blanket and the size and location of the orifices are such that sufficient pressure exists within the blanket to prevent crimping blockage and to insure a uniform flow of air through the orifices throughout the blanket area.

U.S. Pat. No. 5,165,127, issued Nov. 24, 1992, to Nicholson, discloses a heating and cooling blanket apparatus which utilizes a circulating heat transfer fluid.

U.S. Pat. No. 5,265,599, issued Nov. 30, 1993, to Stephenson et al, discloses a patient temperature control blanket with controlled air distribution. The blanket is provided with a plurality of orifices through which controlled pressurized air is introduced upon the patient's body to regulate patient body temperature.

U.S. Pat. No. 5,392,847, issued Feb. 28, 1995, to Stephenson, discloses a thermal medical blanket which distributes heated or cooling air upon the patient.

In 1992, one of the inventors utilized a modified non-commercial embodiment of the RotoRest bed (Kinetic Concepts, Inc.) in an hypothermia study. This bed had been equipped with cooling panels for wrapping the abdomen and chest. Unfortunately, this ted does not have the capability of warming and cooling different body surfaces at the same time, the cooling apparatus cannot be used independently of the bed, and the bed cannot be used in the operating room or post operative room because of limitations imposed on patient care by the RotoRest bed.

However, in spite of these advancements in the prior art, none of these prior art references disclose or suggest, an apparatus for selective rewarming of a hypothermia patient to rewarm various body parts at different rates and at different temperatures to minimize the occurrence of vasodilation. Additionally, none of these prior art references disclose a suit which wraps the torso and legs leaving the arms, buttocks, perineum and head exposed. Furthermore, none of the prior art references disclose panels which may be opened to gain access to the chest, abdomen, legs or backs to expose a surgical field or to provide access to these areas for necessary medical care.

For example, in the situation of a patient suffering from hypothermia or in whom hypothermia has been deliberately induced, exposure of the arms is necessary as they are the primary site for insertion of necessary intravenous lines. Exposure of the head is necessary to maintain control of the airway. The ability to gain ready access to the chest, back and abdomen (the core) is necessary should cardiopulmonary resuscitation be needed, to auscultate heart and breath sounds, to auscultate abdominal sounds or to provide exposure for surgeries of the chest, back or abdomen. Exposure of the legs is necessary for hygiene or for surgery of the legs. The perineum is always exposed in order to provide access at all time to the urinary tract and also) because of the significant hygiene issues associated with these sites where body wastes are eliminated. Firm contact of the blanket to the torso and legs is necessary to control temperature whether inducing hypothermia, maintaining hypothermia or rewarming. In a medical setting however, ready access to the torso and legs and exposure of head arms and perineum is required. None of the devises of the prior art meets these needs.

Thus, there is still a need in the art for apparatus for selective heating and cooling of various body parts of a human suffering from hypothermia so that various body parts can be heated and cooled at different rates and at different temperatures.

There is still another need in the art for an apparatus for heating and cooling of a patient which will also provide for easy access to the patient's body while it is being heated and/or cooled.

These and other needs in the art will become apparent to those of skill in the art upon review of this specification, including its drawings and claims.

SUMMARY OF THE INVENTION

It is an object of the present invention to provide for an apparatus for the selective heating and cooling of a patient so that various body parts can be heated and cooled at different rates and at different temperatures.

It is another object of the present invention to provide for an apparatus for the heating and cooling of a patient which also allows for easy access to various body parts of the patient during such heating and cooling.

These and other objects of the present invention will become apparent to those of skill in the art upon review of this specification, including its drawings and claims.

DETAILED DESCRIPTION OF THE INVENTION

Figure 1:
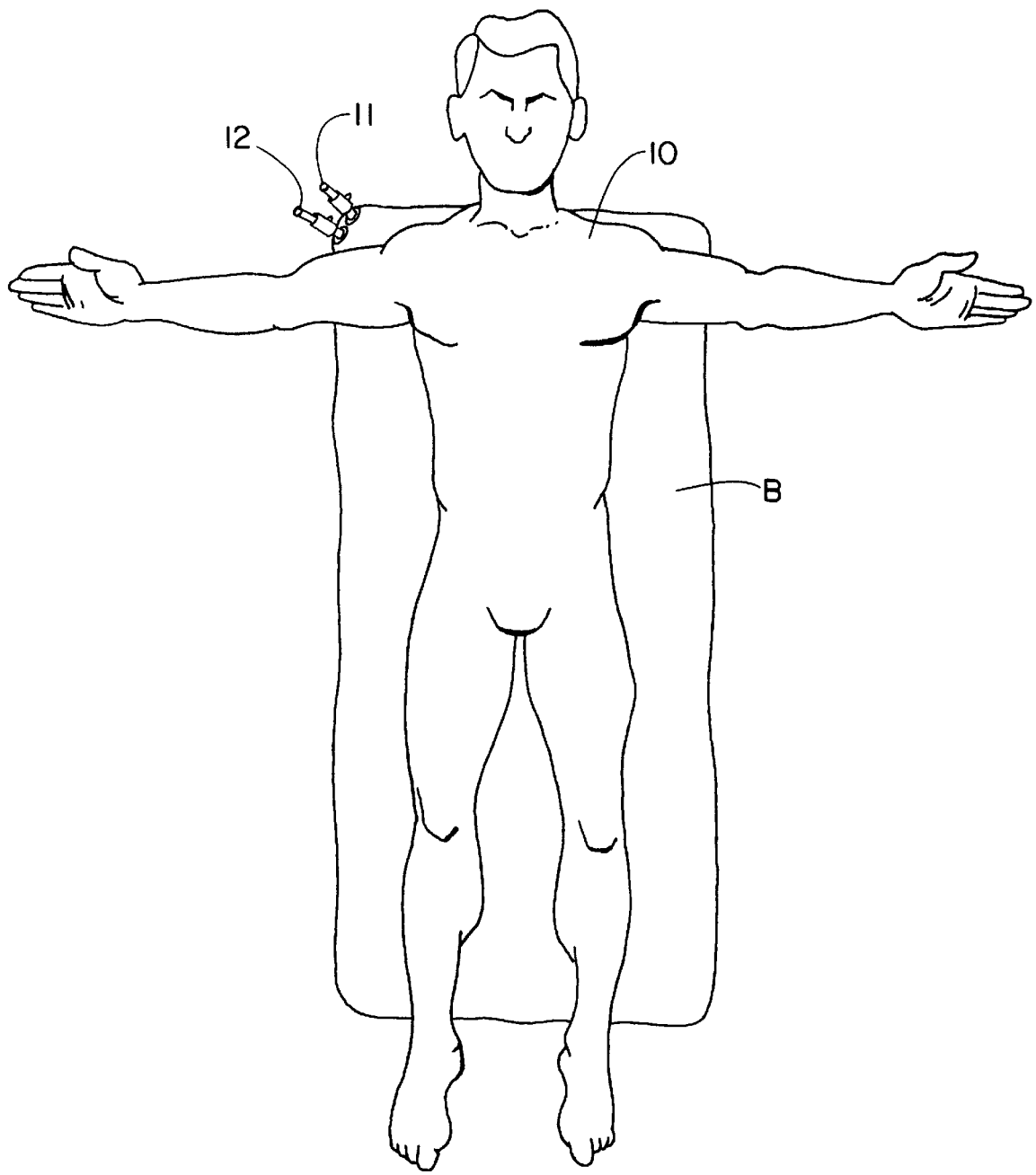
FIG. 1 is an illustration of patient 10 shown positioned on a prior art blanket B.

Prior to discussion of the details of the present invention, reference will first be made to a commonly used prior art blanket. Referring first to FIG. 1, there is shown an illustration of patient 10 shown positioned on a prior art blanket B. The configuration of a prior art blanket shown generally in FIG. 1 is currently the only configuration commercially available. A heat transfer fluid is circulated into and out of blanket B utilizing tubing 11 and 12 respectively. Notice how blanket B generally makes contact with only a limited portion of the skin surface of patient 10, generally the back or front body portion upon which patient 10 is resting. Alternatively, blanket B may be positioned on top of patient 10, but the same limitations apply. In addition, in the operating room where a patient is on his side, prior art blanket 10 would only contact the side of the patient. Furthermore, due to its rectangular shape, prior art blanket 10 cannot wrap the legs or the trunk leaving the majority of the body surface unexposed to the blanket. In any of the above situations, the heat transfer area could be improved.

Figure 2:
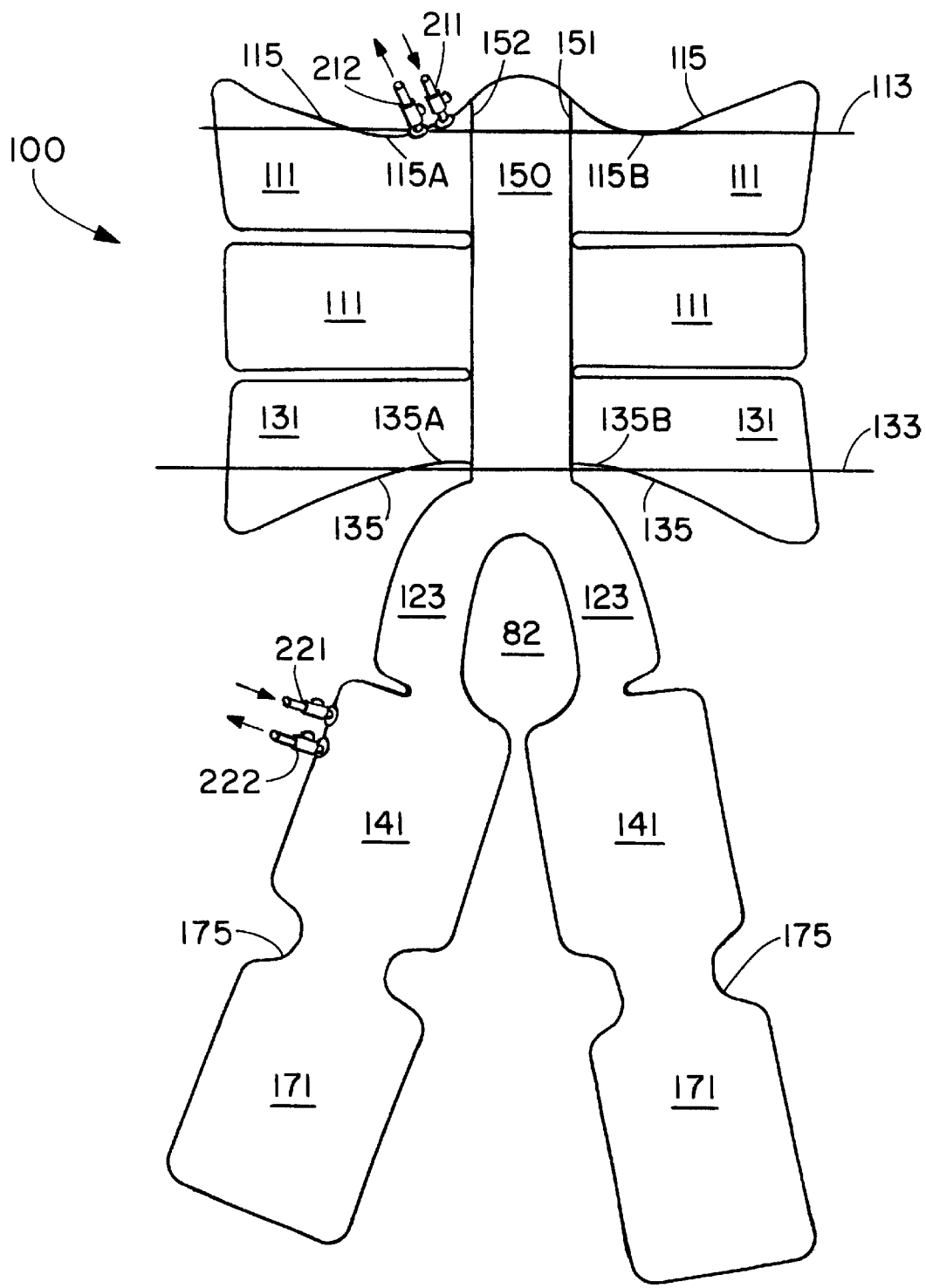
FIG. 2 is an illustration of one embodiment of heating and cooling blanket 100 of the present invention, with chest receiving area 11, abdomen receiving area 31, upper leg receiving areas 41 and lower leg receiving areas 71.

The present invention will now be described by reference to FIGS. 2–9. Referring first to FIG. 2 there is shown one embodiment of heating and cooling blanket 100 of the present invention, with chest receiving areas 11, abdomen receiving area 31, upper leg receiving areas 41 and lower leg receiving areas 71. Heating and cooling blanket 100 provides for the wrapping of the chest, abdomen, and upper and lower legs using various panels 111, 131, 141 and 171, respectively. These various panels may be opened for access during surgery, medical procedures or hygiene.

Figure 3:
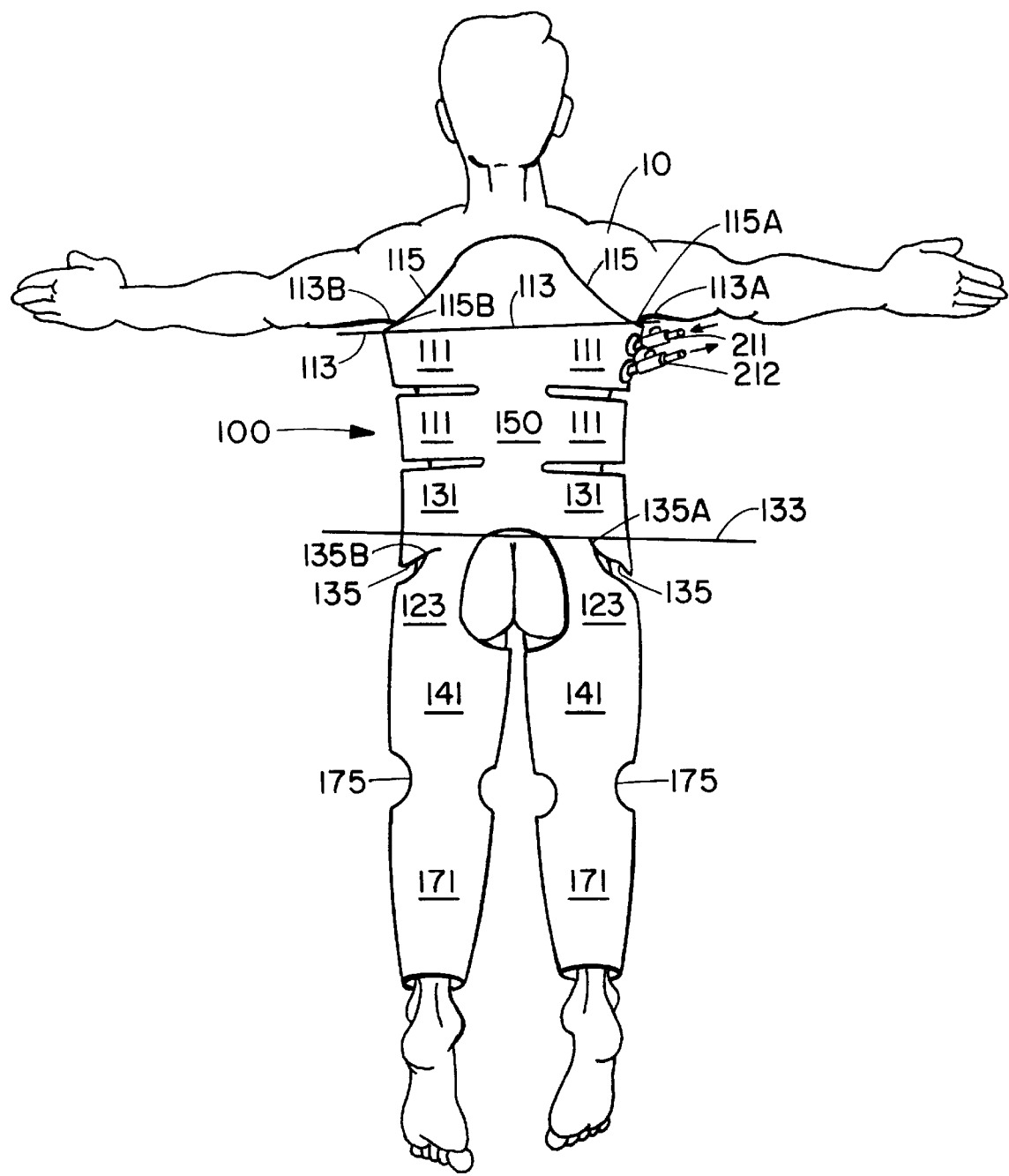
FIGS. 3 and 4, are illustrations showing back and front views, respectively, of patient 10 positioned on heating and cooling blanket 100 with chest panels 111, abdomen panels 131, upper leg panels 141 and lower leg panels 171 wrapping respectively, the chest, abdomen, and upper and lower legs.
Figure 4:
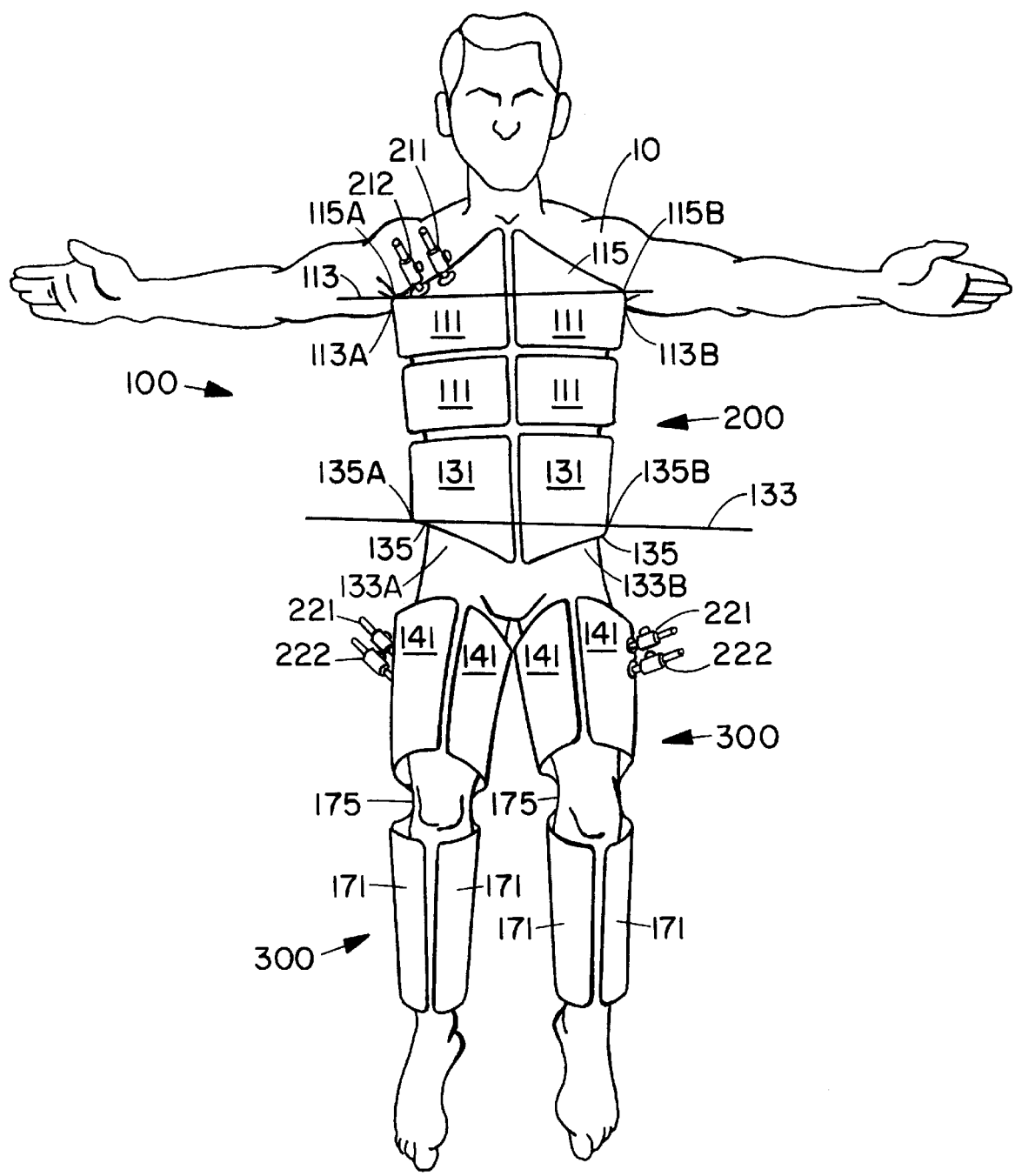

Referring additionally to FIGS. 3 and 4, there are shown back and front views, respectively, of patient 10 positioned on heating and cooling blanket 100 with chest panels 111, abdomen panels 131, upper leg panels 141 and lower leg panels 171 wrapping respectively, the chest, abdomen, and upper and lower legs.

Notice that full access is provided to the head and neck, the arms, the feet, and the perineum. Although not necessary, it is desirable that heating and cooling blanket 100 be reversible, that is, that patient 10 may be placed on the top or bottom of blanket 100. This is important in the operating room when access to the back is necessary, but the chest and legs require coverage with the blanket parts.

Referring to FIG. 2, central panel 150 is provided so that in the lateral position during surgery heating and cooling blanket 100 may optionally be used with one or more panels opened, providing full access to the thorax and the flanks for surgery. Central panel 150 generally extends from the neck to the buttocks and is bounded by fold lines 151 and 152, with the distance between fold lines in the range of about 2 to about 12 inches, preferably in the range of about 4 to about 6 inches.

Figure 5:
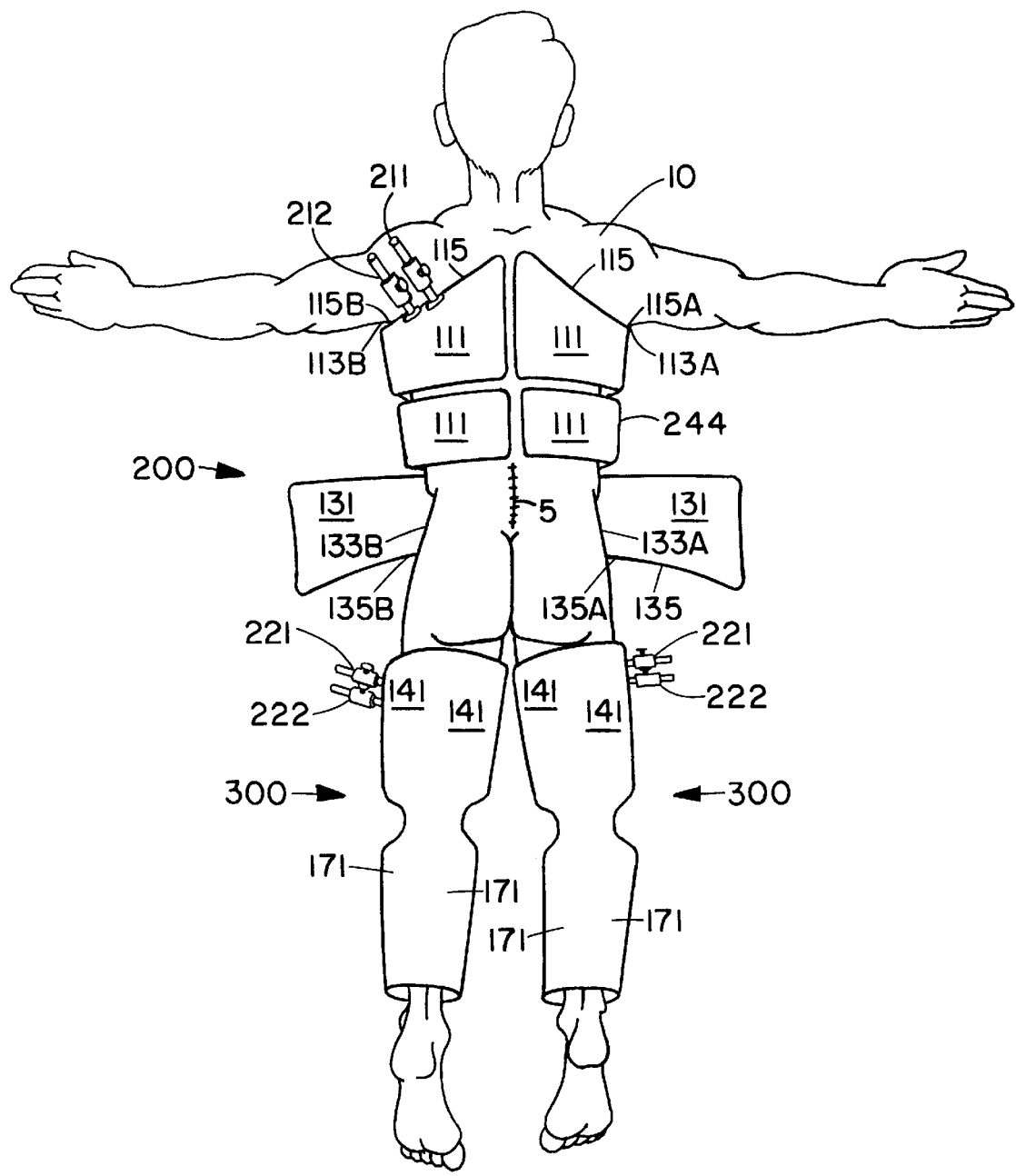
FIG. 5 is an illustration showing patient 10 positioned on heating and cooling blanket 100 with abdomen panels 131 opened to allow for surgical access to patient's back 5.

Referring additionally to FIG. 5, there is shown patient 10 positioned on heating and cooling blanket 100 with abdomen panels 131 opened to allow for surgical access to patient's back 5. Alternatively, the other various panels 111, 141 and/or 171 could likewise be opened as necessary or desired.

Figure 6:
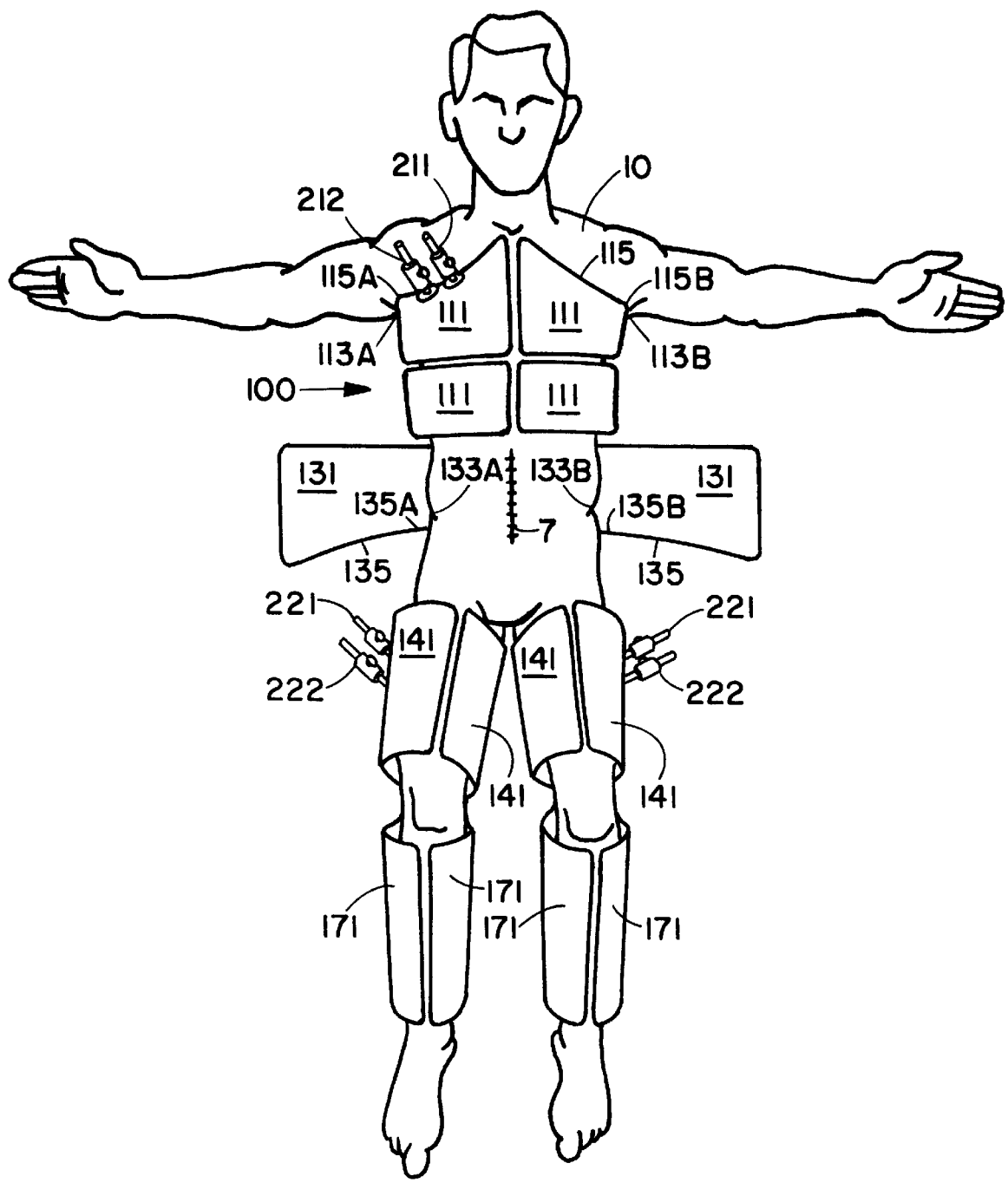
FIG. 6 is an illustration showing patient 10 positioned on heating and cooling blanket 100 with abdomen panels 131 opened to allow for surgical access to patient's abdomen 7.

Referring now additionally to FIG. 6 there is shown an illustration showing patient 10 positioned on heating and cooling blanket 100 with abdomen panels 131 opened to allow for surgical access to patients abdomen 7. Alternatively, the other various panels 111, 141 and/or 171 could likewise be opened as necessary or desired.

Figure 7:
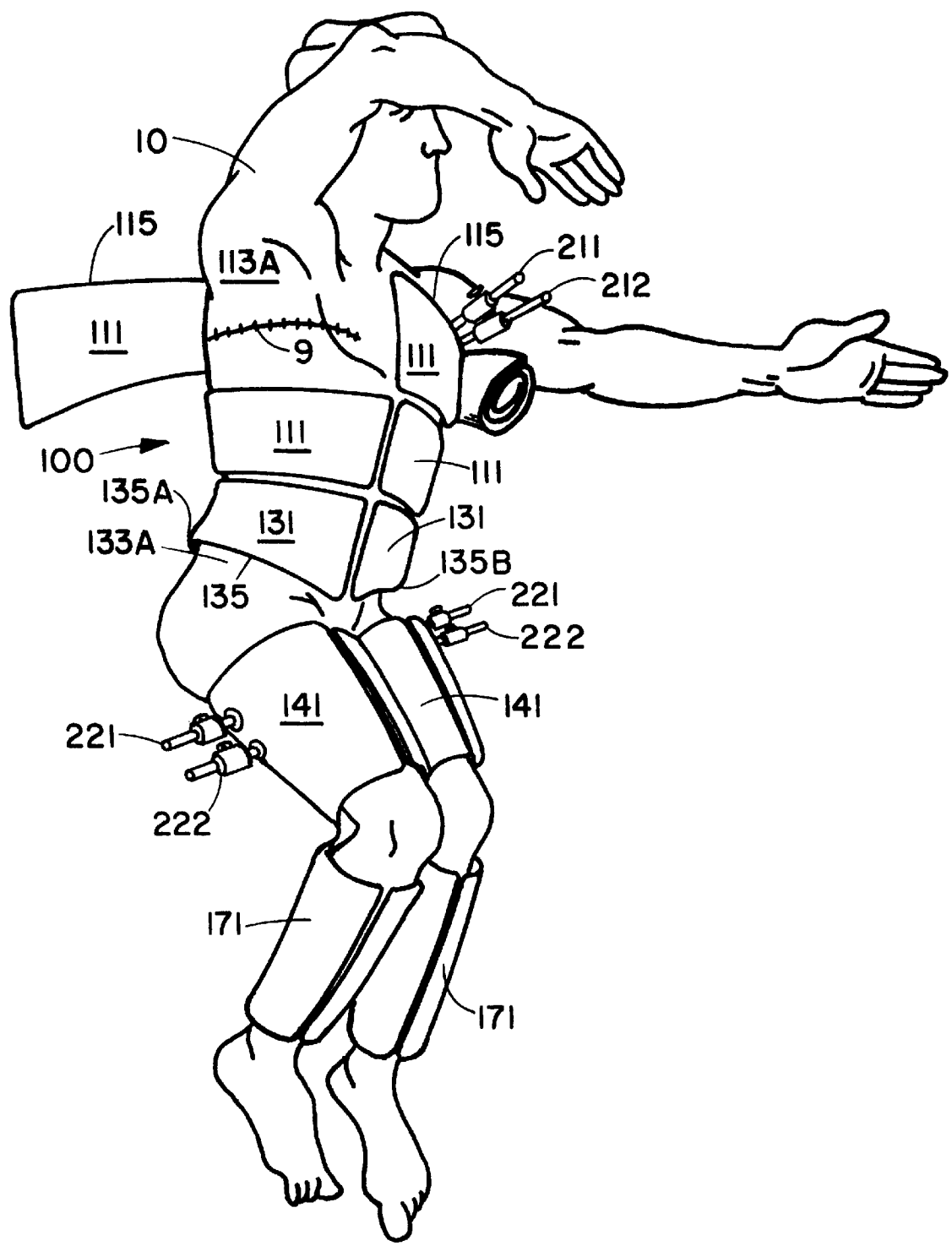
FIG. 7 is an illustration showing patient 10 in a lateral position on heating and cooling blanket 100 with with chest panel 111 open to expose the upper right portion of patient's chest 9.

Referring now additionally to FIG. 7 there is shown an illustration of patient 10 in a lateral position on heating and cooling blanket 100 with chest panel 111 open to expose the upper right portion of patient's chest 9. Alternatively, the other various panels 131, 141 and/or 171 could likewise be opened as necessary or desired.

It is generally desirable to provide for spacing between chest panels 111 and abdomen panels 131, to allow for access to the abdomen during laparotomy. While in the embodiment as shown, only the upper edge of chest panels 111 are tapered, this may be accomplished by providing one or both of the panels 111 and 131 with a slight taper or angle to provide for spacing between panels 111 and 131.

As shown in FIG. 2, perineum opening 82 provides both anterior and posterior access at the perineum for hygiene and for catheter egress. Alternatively, heating and cooling blanket 100 of the present invention may be provided with a disposable surface at the perineum to prevent soiling of blanket 100.

Heating and cooling apparatus 100 of the present invention may be provided with a heat transfer fluid to allow for heating or cooling. Generally, a heat transfer fluid, most commonly water, is circulates through heating and cooling blanket 100 which is generally provided with internal passages, tubing, channels or the like. This heat transfer fluid is provided at a desired temperature, and is circulated at a desired rate to provide the desired heating or cooling to patient 10.

The entire heating and cooling blanket 100 may consist of a single fluid communication zone. Such an arrangement would provide essentially a single temperature throughout, with minor temperature deviations depending upon the fluid flow patterns.

Alternatively, heating and cooling blanket 100 could be provided with two or more fluid communication zones which may be independently heated and/or cooled as desired. For example, each of panels 111, 131, 141 and 171 could be provided with independent fluid circulation and independently heated and/or cooled as desired. As another example, for those surgical procedures requiring the temperature of the upper body to be independently controlled from that of the lower body, upper body chest panels 111 and abdomen panels 131 could be in fluid communication with each other, and lower body upper leg panels 141 and lower leg panels 131 could be in communication with each other, with the upper and lower body panels not in fluid communication.

Each fluid communication zone that is to be heated and/or cooled will include internal channels, passages tubing or the like, for receiving a heat transfer medium which will be passed through the zone to provide heating or cooling. For example, the heating and cooling zones may be provided with one or more medium carrying conduits through which a heat transfer medium can flow. Alternatively, each of the heat transfer zones, may be provided with a plurality of passages forming a crisscross waffle grid pattern for the random flow of the heat transfer medium in many directions within each of the heat transfer zones as is disclosed in U.S. Pat. No. 4,149,541, issued Apr. 17, 1979 to Gammons, et al, the disclosure of which is herein incorporated by reference.

The various fluid communication zones of the heating and cooling apparatus 100 of the present invention include heat transfer inlets for introducing the heat transfer medium to the respective zone, and a heat transfer medium outlet through which the heat transfer medium exits the various heating and cooling zones. Generally, the heat transfer medium inlet and the heat transfer medium outlet comprise a screw fit, snap fit or other type of friction fit mechanism for engagement with tubing, piping, hosing or other type of conduit which will provide a heat transfer medium to the heat transfer zone and carry such heat transfer medium away from the heat transfer zone.

It is generally desired that at least one set of heat transfer medium inlets and the heat transfer medium outlets be positioned on one side of heating and cooling blanket 100, because generally, the direction from which the fluid is provided will generally also be the direction for return. Preferably, at least one set of heat transfer medium inlets and the heat transfer medium outlets be positioned on each side of heating and cooling blanket 100, because generally in the haste of positioning blanket 100, care may not have been taken to determine the locations of the source of heat transfer fluid. Such an arrangement will maintain the reversible nature of using blanket 100.

For example, in the embodiment as shown in FIGS. 2–5, upper body chest panels 111 and abdomen panels 131 are in fluid communication with each other with heat transfer fluid provided through tubing 211 and returning through tubing 212. The heat transfer fluid enters through tubing 211 circulates through body chest panels 111 and abdomen panels 131 and returns through tubing 212. Likewise, lower body upper leg panels 141 and lower leg panels 171 are in communication with each other. Heat transfer fluid enters through tubing 221, circulates through panels 141 and 171 and returns through tubing 222. Slightly different, non-limiting alternative positioning embodiments for tubing 211 and 212 and tubing 221 and 222 are shown in FIGS. 2–7.

It is also generally desirable that the internal fluid communication of blanket 100 be suitable to allow for panels to be folded back on themselves without substantially impeding fluid flow. This is generally accomplished by utilizing fluid passages having suitable amount of structural integrity to resist collapse, and by using a multiplicity of passages to provide alternate fluid communication routes.

It must be understood that while one or two zones are illustrated in the heating and cooling blanket embodiment as shown in FIGS. 2–5, any desired number of zone(s) may be utilized in the practice of the present invention.

As an alternate mode of operating the heating and cooling blanket embodiment as shown in FIGS. 2–5, the outlet tubing 212 could be connected with inlet tubing 221 to convert this two zone embodiment into a single fluid communication zone embodiment.

In the practice of the present invention, the heat transfer medium utilized may be any suitable liquid, gas, gel, foam, emulsion or other flowable medium which is suitable for heat transfer. Preferably, the heat transfer medium utilized in the present invention is water. It should be understood that the heat transfer medium utilized in the present invention may include other substances, such as preservatives, bacteriacides, odorants, coloring agents, anti-corrosion agents, anti-oxidants, surfactants, sealants, and the like.

In the practice of the present invention, each of the panels may be held in place by their own weight, by adhesive tape, or by the use of any suitable fastener including snaps, buttons, hooks, zippers, and hook and loop type systems a commercially available example of which includes VELCRO.

Heating and cooling apparatus 100 of the present invention may optionally be provided one or more access points for gaining access to a specific portion of the body of patient 10. For example, any of the panels may be provided with smaller sized openable or removable panels to allow access to patient 10 without the need to open or remove the larger panel. Each of these smaller sized panels may be secured in place by their own weight, with adhesive tape, or by any suitable fastener including snaps, buttons, hooks, zippers, and hock and loop type systems a commercially available example which includes VELCRO.

Optionally, any part of heating and cooling blanket 100 may be transparent to permit visual observation of the underlying body without removal of blanket 100.

The heat transfer medium of the present invention may be circulated through a closed loop heating or cooling system which is positioned adjacent to the heating and cooling apparatus 100 of the present invention. Methods of an apparatus for heating and cooling a circulating heat transfer medium are well known, and the present invention is not to be limited in any particular type of system. Alternatively, heat transfer medium may be provided from a larger system, such as a hospital heating or cooling eater system.

It is envisioned that any suitable materials of construction may be utilized in the construction of the heating and cooling apparatus 100 of the present invention. In most instances, the range of operating temperatures will be those that which water is in the liquid state. It is generally preferred that the material of construction not be too resistant to bending and folding at colder temperatures. In general, the materials of construction will generally be selected from among thermoplastics, thermosets, elastomers, and rubbers.

The surface of heating and cooling blanket 100 which contacts patient 10 preferably comprises an absorbent material.

It must be understood that while the heating and cooling blanket 100 of the present invention has be illustrated only with panels for the chest, abdomen, and upper and lower legs, other panels for the head, neck, arms, hands and feet may optionally be utilized as desired or needed. Additionally, any suitable combination of panels covering any desired portion(s) of patient 10 may be utilized.

Figure 8:
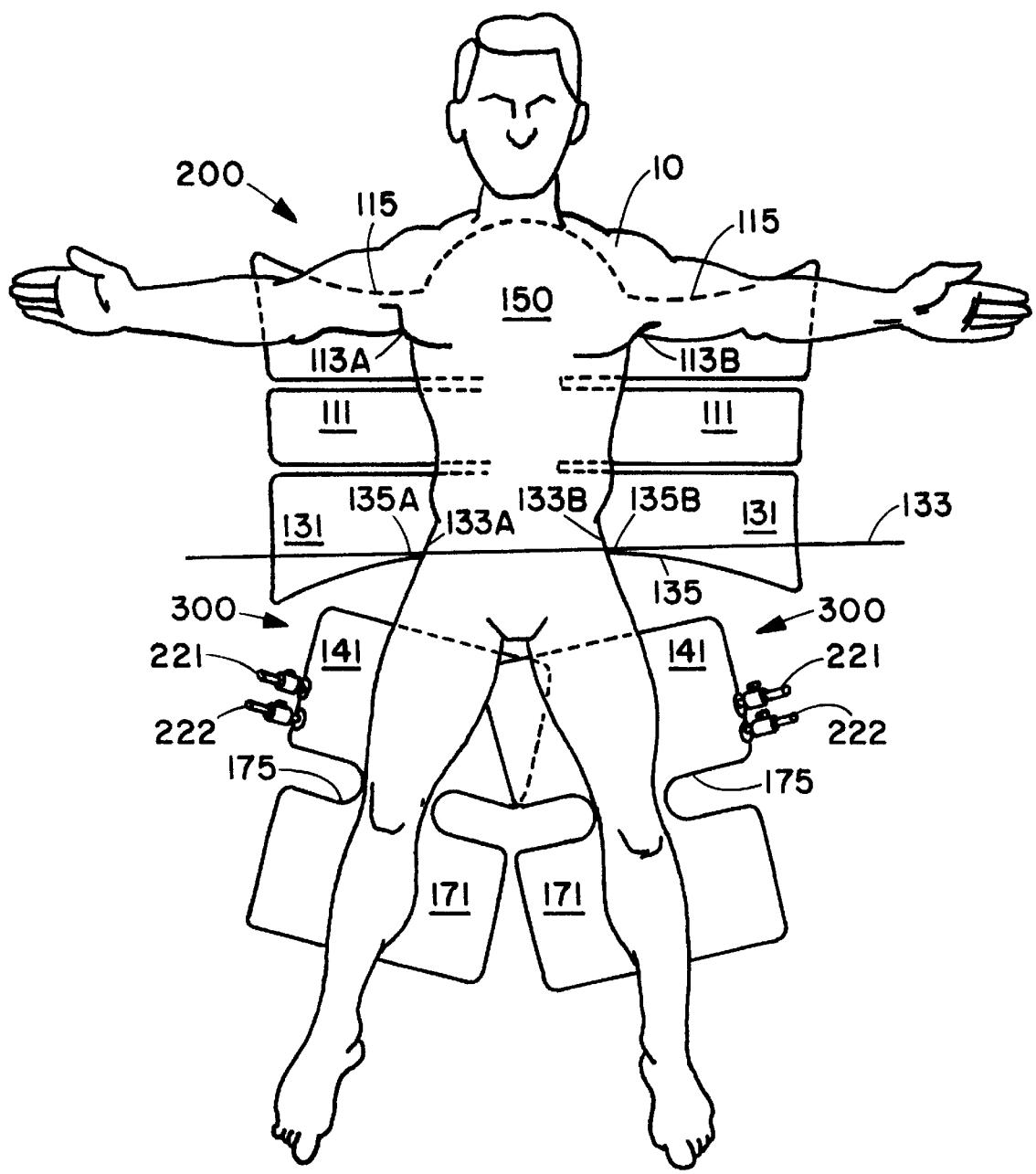
FIG. 8 is an illustration of another embodiment of heating and cooling blanket 100 of the present invention, showing patient 10 wrapped in cooling blanket 100 where leg wraps 240 and 242 are independent of each other and of torso wrap 244.
Figure 9:
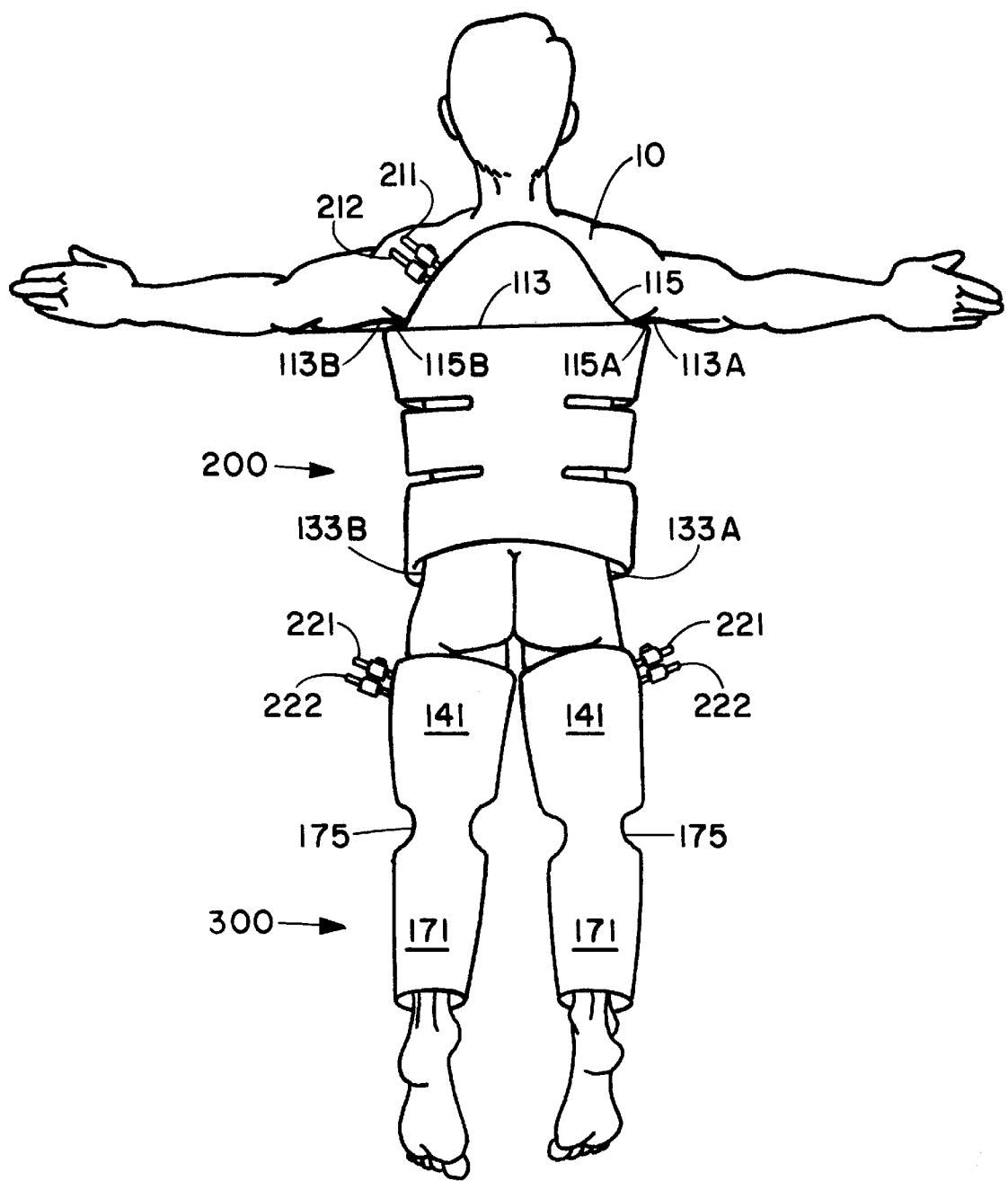
FIG. 9 is an illustration showing a back view of patient 10 positioned on the heating and cooling blanket 100 of FIG. 8 where leg wraps 240 and 242 are independent of each other and of torso wrap 244. The anterior view of FIG. 9 is the same as shown in FIG. 4.

Referring now to FIG. 8 there is shown an illustration of another embodiment of heating and cooling blanket 100 of the present invention where leg wraps 240 and 242 are independent of each other and of torso wrap 244. Cooled fluid or air may be provided to each unit separately. Referring now to FIG. 9, there is shown a back view of patient 10 positioned on the heating and cooling blanket 100 of FIG. 8, where leg wraps 240 and 242 are independent of each other and of torso wrap 244.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

I claim:

1. An apparatus for providing heating and cooling to a human body having a perineum, chest, abdomen and legs, the apparatus comprising:
    (a) a main panel for receiving the body, wherein the main panel defines a passage for gaining access to the perineum, and further defines a main panel fluid circulation path within the panel;
    (b) at least one chest panel connected to the main panel, wherein the chest panel is suitable for wrapping the chest of the body, and wherein the chest panel further defines a chest panel fluid circulation path within the panel;

(c) at least one leg panel connected to the main panel, wherein the leg panel is suitable for wrapping at least one of the legs of the body, and wherein the leg panel further defines a leg panel fluid circulation path within the panel;

(d) at least one abdomen panel connected to the main panel, wherein the abdomen panel is suitable for wrapping the abdomen of the body, and wherein the abdomen panel further defines an abdomen panel fluid circulation path within the panel;

(e) a fluid communication system providing fluid communication between the fluid circulation paths of the panels, and having an inlet and an outlet, wherein the fluid is not in direct contact with the human body.

2. The apparatus of claim 1 wherein a heat transfer medium is circulated through the fluid communication system.

3. The apparatus of claim 2 wherein tie heat transfer medium is water.

4. The apparatus of claim 1 wherein the fluid communication system is provided with a plurality of passages forming a crisscross waffle grid pattern for the random flow of the heat transfer medium.

5. The apparatus of claim 1 wherein the inlet and outlet further comprise a mechanism for engagement with a conduit for the heat transfer medium.

6. The apparatus of claim 1 wherein the panels are held in place by a fastener selected from the group consisting of snaps buttons, hooks, zippers, and hook and loop type systems.

7. The apparatus of claim 1 where the passage for gaining access to the perineum is provided with a disposable surface.

8. An apparatus for providing heating and cooling to a human body having a perineum, chest, abdomen and legs, the apparatus comprising:

(a) a main panel for receiving the body, wherein the main panel defines a passage for gaining access to the perineum, and further defines a main panel fluid circulation path within the panel;

(b) at least one chest panel connected to the main panel, wherein the chest panel is suitable for wrapping the chest of the body, and wherein the chest panel further defines a chest panel fluid circulation path within the panel;

(c) at least one leg panel connected to the main panel, wherein the leg panel is suitable for wrapping at least one of the legs of the body, and wherein the leg panel further defines a leg panel fluid circulation path within the panel;

(d) at least one abdomen panel connected to the main panel, wherein the abdomen panel is suitable for wrapping the abdomen of the body, and wherein the abdomen panel further defines an abdomen panel fluid circulation path within the panel;

(e) a first fluid communication system providing fluid communication between the fluid circulation paths of the chest and abdomen panels, and having an inlet and an outlet, wherein the fluid is not in direct contact with the human body;

(f) a second fluid communication system providing fluid communication in the leg panel fluid circulation path, and having an inlet and an outlet, wherein the fluid is not in direct contact with the human body.

9. The apparatus of claim 8 wherein a first heat transfer medium is circulated through the first fluid communication system and a second heat transfer medium is circulated through the second fluid communication system.

10. The apparatus of claim 9 wherein the heat transfer medium is water.

11. The apparatus of claim 8 wherein the fluid communication system is provided with a plurality of passages forming a crisscross waffle grid pattern for the random flow of the heat transfer medium.

12. The apparatus of claim 8 wherein the inlet and outlet further comprise a mechanism for engagement with a conduit for the heat transfer medium.

13. The apparatus of claim 8 wherein the panels are held in place by a fastener selected from the (group consisting of snaps buttons, hooks, zippers, and hook and loop type systems.

14. The apparatus of claim 8 where the passage for gaining access to the perineum is provided with a disposable surface.

15. An apparatus for providing heating and cooling to a human body having a perineum, chest, abdomen and legs, the apparatus comprising:

(a) a main panel for receiving the body, wherein the main panel defines a passage for gaining access to the perineum;

(b) at least one chest panel connected to the main panel, wherein the chest panel is suitable for wrapping the chest of the body, wherein the panel further comprises a fluid communication system for circulating a heat transfer fluid in the panel, and wherein the fluid is not in direct contact with the human body;

(c) at least one leg panel connected to the main panel, wherein the leg panel is suitable for wrapping at least one of the legs of the body, wherein the panel further comprises a fluid communication system for circulating a heat transfer fluid in the panel, and wherein the fluid is not in direct contact with the human body;

(d) at least one abdomen panel connected to the main panel, wherein the abdomen panel is suitable for wrapping the abdomen of the body, wherein the panel further comprises a fluid communication system for circulating a heat transfer fluid in the panel, and wherein the fluid is not in direct contact with the human body.

16. The apparatus of claim 15 wherein the heat transfer fluid is water.

17. The apparatus of claim 15 wherein the fluid communication system is provided with a plurality of passages forming a crisscross waffle grid pattern for the random flow of the heat transfer medium.

18. The apparatus of claim 15 wherein the inlet and outlet further comprise a mechanism for engagement with a conduit for the heat transfer fluid.

19. The apparatus of claim 15 wherein the panels are held in place by a fastener selected from the group consisting of snaps buttons, hooks, zippers, and hook and loop type systems.

20. The apparatus of claim 13 where the passage for gaining access to the perineum is provided with a disposable surface.

* * * * *